United States Patent [19]

Freiser et al.

[11] 4,115,209

[45] Sep. 19, 1978

[54] METHOD OF DETERMINING ION ACTIVITY USING COATED ION SELECTIVE ELECTRODES

[75] Inventors: Henry Freiser, Tucson, Ariz.; Helen J. James, Ogden, Utah; Gary Carmack, Tuscon, Ariz.; Robert W. Cattrall, Victoria, Australia; Barbara M. Kneebone, Tucson, Ariz.

[73] Assignee: Research Corporation, New York, N.Y.

[21] Appl. No.: 844,146

[22] Filed: Oct. 20, 1977

Related U.S. Application Data

[63] Continuation of Ser. No. 519,297, Oct. 30, 1974, abandoned, which is a continuation-in-part of Ser. No. 219,119, Jan. 19, 1972, abandoned.

[51] Int. Cl.$^2$ ............................................. G01N 27/46
[52] U.S. Cl. ................................. 204/1 T; 204/195 M
[58] Field of Search ............................ 204/195 M, 1 T

[56] References Cited

U.S. PATENT DOCUMENTS

| Re. 24,222 | 9/1956 | Patnode et al. | 204/195 M |
|---|---|---|---|
| 3,446,726 | 5/1969 | Pungor et al. | 204/195 M X |
| 3,607,710 | 9/1971 | Farren et al. | 204/195 M |
| 3,691,047 | 9/1972 | Ross et al. | 204/195 M |
| 3,706,649 | 12/1972 | Cosgrove et al. | 204/195 M |
| 3,767,553 | 10/1973 | Brown et al. | 204/195 M |
| 3,787,309 | 1/1974 | Neti et al. | 204/195 M |
| 3,811,184 | 5/1974 | Niedrach et al. | 204/195 M X |
| 3,822,199 | 7/1974 | Luck et al. | 204/195 M |
| 3,843,490 | 10/1974 | Higuchi | 204/1 T |

FOREIGN PATENT DOCUMENTS

| 763,082 | 7/1967 | Canada | 204/195 M |
|---|---|---|---|
| 2,027,128 | 12/1970 | Fed. Rep. of Germany | 204/195 M |

OTHER PUBLICATIONS

R. W. Cattrall et al., Anal. Chem., vol. 43, No. 13, pp. 1905–1906, (1971).

*Primary Examiner*—G. L. Kaplan
*Attorney, Agent, or Firm*—Oblon, Fisher, Spivak, McClelland & Maier

[57] ABSTRACT

The potentiometric responses caused by ion activity changes in solution are measured with an electrode formed by coating an ion exchange material which is molecularly dispersed throughout an insoluble film-forming polymeric matrix directly onto a conductive substrate such that an oxidation-reduction mechanism is not operative in the response of said electrode to the activity of ions in said solution.

7 Claims, No Drawings

METHOD OF DETERMINING ION ACTIVITY USING COATED ION SELECTIVE ELECTRODES

CROSS-REFERENCE TO RELATED APPLICATIONS

This is a continuation of application Ser. No. 519,297, filed Oct. 30, 1974 which in turn was a continuation-in-part of application Ser. No. 219,119, filed Jan. 19, 1972, both now abandoned.

BACKGROUND OF THE INVENTION

1. Field of the Invention

This invention relates to ion selective electrodes, and more particularly to an electrode formed by coating a conductor with an ion exchange material.

2. Description of the Prior Art

In general, there are two types of electrodes in conventional use. The first, and simplest, are those prepared with fine metallic wires, such as Ag and Cu, which respond to activity changes in $Ag^+$ or $Cu^{++}$, respectively. Unfortunately, these types of electrodes are only available for a very limited number of ions.

A wider variety of ions give potentiometric responses to a second type of electrode, in which a metal wire is coated with a poorly soluble salt of the metal, such as an Ag/AgCl electrode, which responds to activity changes in $Cl^-$.

Membrane electrodes, which are highly selective to various ions, are well known in the prior art. Usually, these types of electrodes consist of a conductive electrode immersed in an aqueous reference solution, which is in contact with a "membrane" or permeable barrier. An interface is formed between the permeable barrier and the test solution which enables potentiometric measurements of the test solution. Probably the oldest and most established example of a membrane electrode is the glass electrode, universally used for pH measurements. More recently available (Orion and Corning) membrane electrodes involve a layer of a liquid which is immiscible with water as a "membrane."

There are many difficulties attendant to the use of commercially available membrane electrodes. For one, they are rather bulky in size, and, hence, are not completely adaptable for many applications. In particular, a need exists for a miniaturized version of the membrane electrode for possible use in ultramicroanalytical situations, including possibly intracellular measurements. Another difficulty with those commercially available electrodes is that their use of a free flowing internal reference solution limits their physical orientation; that is, they cannot be used in an inverted position, since the reference solution will spill out of the electrode.

Another difficulty with the conventional membrane electrodes is that they are somewhat complex in structure and hence are very expensive to produce and frequently expensive to maintain and to protect from breakage.

One approach to production of a solid state membrane type electrode, which might be adaptable to miniaturization, has been disclosed by Hirata et al. in *Talanta,* 1970, Vol. 17, Page 883, which disclosed the feasibility of affixing a membrane directly to a non-reactive metal wire, thus eliminating the internal reference solution. According to that disclosure, a $Cu^{++}$ selective electrode was produced by attaching a $Cu_2S$-impregnated silicone rubber or epoxy resin membrane to either a copper plate or a platinum wire. Although that electrode is considerably less bulky than the prior art membrane electrodes, it suffers the disadvantage that poor results are obtained unless the membrane is loaded with sufficient $Cu_2S$, so that the $Cu_2S$ particles are in sufficient mutual contact to establish lines of conductivity from the surface of the membrane to the non-reactive metal. This type of electrode, therefore, might be considered to be merely a modification of a $Cu/Cu_2S$ precipitate type electrode, wherein a layer of Cu is in contact with a layer of $Cu_2S$.

Moreover, the Hirata et al. electrode is limited in the type of salts which can be incorporated therein. As is well known, the usefulness of a particular electrode depends upon the particular potentiometrically responsive ion contained in the system. For instance, a $Cu/Cu_2S$ electrode can only be used to measure activity changes in Cu ions or sulfide ions. When other measurements or titrations are required, different electrode systems are necessary. The Hirata et al. electrode is therefore limited to those systems for which a suitable combination of metal-metal salts can be formed; that is, given the type of ion, a suitable slightly soluble salt must be found to form the metal/metal salt precipitate type system. Such suitable salts, however, are not always available.

Another approach to solid state membrane type electrodes has been disclosed by M. R. Thompson, *Journal of Research of the National Bureau of Standards* 9, 833 (1932), in which a thin metal film is plated onto the inside of an otherwise conventional glass, as a replacement for the internal reference solution. That system is similarly limited as the Hirata et al. system, in the variety of ion selective electrodes which can be formed.

It would be desirable, therefore, to provide an electrode of low bulk, which can be easily miniaturized, which has a high degree of uniformity in response, is easily manufacturable and which can easily be adapted for potentiometric measurement of a wide variety of ions.

SUMMARY OF THE INVENTION

Accordingly, it is one object of this invention to provide a membrane type electrode which does not use an internal reference solution, and hence is less bulky and more adaptable to miniaturization than previously available membrane type electrodes.

It is another object of this invention to provide membrane type electrodes for use with any of a large variety of ions.

Still another object of this invention is to provide a membrane type electrode which can provide a highly reproducible and sensitive response.

A further object of this invention is to provide a membrane type electrode which would be considerably less expensive and less complicated to produce than presently commercially available electrodes.

These and other objects have now herein been attained by providing an electrode of a conductive substrate which is coated with an ion exchange material in a suitable matrix. The coating may consist of a polymeric matrix containing a molecular dispersion of the ion exchange material. Electrodes of this type have been shown to provide rapid, reproducible responses of high selectivity, which equal or excel the responses and selectiveness obtained with prior art membrane electrodes, which use internal reference solutions. The mechanism by which the electrode responds to ion activity in solution does not involve an oxidation-reduction electron exchange. By the term "molecular dispersion" is meant a true solution, or the use of an ion exchange resin.

DETAILED DESCRIPTION OF THE PREFERRED EMBODIMENTS

According to the present invention, a membrane type electrode is provided by coating an ion exchange material in a suitable matrix onto a conductive substrate.

In the usual electrode measurement system, the testing electrode is wired through a potentiometer to a reference electrode, usually a calomel electrode, to form a full cell circuit. When the cell is used to control or measure a titration operation, activity changes in the measured ions are shown as changes in the E.M.F. of the cell.

In selecting a suitable substrate for the electrode of the present invention, therefore, it is only necessary that the substrate be capable of being wired to a potentiometer. Aside from this limitation, any electrically conductive substrate in almost any form may be used. Although the most convenient form of the substrate will usually be a fine wire, the substrate may take the form of a self-supporting sheet or film, or a coating on a non-conductive base sub-support.

Any conductive metal, such as Cu, Pt, Ag, Au, or the like, or carbon, may be used in forming the conductive substrate.

The ion exchange material may contain any potentiometrically measurable ion or group of ions, and it may be either cationic or anionic. Suitable exchange materials are the quaternary alkyl, aryl, or aralkyl ammonium, phosphonium, arsonium, stibonium or sulfonium ions. Other suitable cations include the various metal ions in simple salts or in neutral or electrically charged chelates or similar complexes, such as those of dithizone, phosphoric acid esters and 8-hydroxyquinoline or the alkyl or halogenated derivatives thereof, or the analogs, such as the mercaptan analog thereof; the long chain aliphatic mercaptans, the alkylated phenols or the macrocyclic ethers, such as the "crown" ethers. It is also possible to prepare potassium or cesium responsive coated electrodes in which the potassium or other alkali metal ions, such as cesium complexes of the crown ethers or analogous compounds, such as valinomycin are incorporated.

Many of the di-, tri- or tetravalent metal ions can also be used in this electrode system. Naturally, as the charge of the metal ion increases, the number of millivolts change per tenfold change in concentration decreases in accord with the prediction from the Nernst equation.

Other cation sensitive material include the metal chelates of dialkyl dithiocarbamates, dithiophosphates, arylarsonic acids, $\beta$-diketones, toluene-3,4-dithiol, glyoxal bis(2-hydroxyanil), phenanthrolines and polypyridyls, tetraalkyl methylenediphosphonates, long chain alkyl or aralkyl mercaptans or oximes, 8-mercaptoquinoline and substituted derivatives thereof.

Suitable anions include chloride, bromide, thiocyanate, oxalate, sulfate, salicylate, perchlorate, iodide, alkyl or aryl sulfonates, acetate, benzoate, nitrate, and amino acid anions, such as phenylaniline and leucine. Other anion sensitive materials include the salts of long chain primary, secondary, and tertiary amines as well as various classes of cationic dyes, such as those of the triphenylmethane types, substituted guanidines, Nile blue or safranine.

Examples of suitable ion exchange salts and materials include: calcium dodecylphosphate, metal salts of acidic phosphate esters such as calcium, nickel, copper, zinc, lanthanum, silver, cadmium, or mercury, di decylphosphate or di(2-ethylhexyl)phosphate or any of the other chelating agents listed above. Similarly for anion exchange materials the following examples of salts and materials would apply: methyltricaprylylammonium perchlorate, nitrate, iodide, bromide, chloride, thiocyanate, acetate, propionate, benzoate, substituted benzoates, arylsulfonates. In place of the methyltricaprylylammonium, the following other cations could be coupled with the same or a selection of the anions listed above: high molecular weight quaternary ammonium, phosphonium, arsonium, stibonium or sulfonium ions, as well as the cations of triphenylmethane dyes, the cationic complex of phenanthroline or substituted phenanthrolines with nickel, iron or copper.

It is well known that when a metal conductor such as platinum wire is placed in a solution for potentiometric measurements that is not heavily dosed with components of an oxidation-reduction system, the potential of the electrode will drift very badly and continuously. However, in potentiometric measurements with the electrode of the present invention, the response of the electrode to ion activity in solution does not involve an oxidation-reduction mechanism. In other words, the electrode is directly responsive to the particular ion being measured in solution.

In one embodiment of this invention, the ion exchange material is incorporated into a polymeric matrix as a true solution or colloidal dispersion in amounts of from 1–25% by weight and preferably 10–25% by weight. In this technique, an ion exchange salt is dissolved in a solvent and the solution is admixed with the binder polymer. The conductive substrate is then coated with the composition, and the solvent is removed. Suitable solvents useful for dissolving the ion exchange salts include the alcohols, such as isoamyl alcohol, benzyl alcohol, decanol; ketones, such as cyclohexanone; esters such as methyl acetate, tributyl phosphate; cyclic ethers, such as tetrahydrofuran, or almost any solvent which is miscible with the solution of the polymeric material used.

Any film forming polymeric material or any material which is capable of being polymerized into a film forming material, or any material which is cross-linkable into a polymeric film, may be used as the binder matrix. For instance, suitable polymeric materials include those polymers or copolymers formed from ethylenically unsaturated monomers, such as the polyolefins, the polyacrylates, the polyvinylhalides, the polyvinylidene halides, the polyacetates, polystyrene or the like, or those polymers formed by condensation techniques, such as the epoxy resins, the polyurethanes, the phenolic resins and the formaldehyde resins, or the like. These polymers can be used per se, or can be used in the form of polymerizable monomers which are subsequently polymerized into the film forming polymer or resin. Specific examples of suitable polymers include polystyrene, polyvinyl chloride, polymethyl methacrylate, the epoxy resins, the polyethylenes, and the like.

A plasticizer may be used with the polymer or polymerizable material to attain a more homogeneous mixture of dispersion. For this purpose, a wide variety of plasticizers may be used. It is most desirable that the plasticizer, however, be selected so that it is compatible with both the polymer and the ion exchange salt and to reduce the electrical resistance of the polymeric bead film. Suitable plasticizers which may be used, depending upon the particular polymer of polymerizable material, include cyclohexanone, dioctyl phosphonate, tributyl phosphate, isoamyl alcohol, n-decanol, dipentyl phthalate, dioctyl and diphenyl phthalates. When a plasticizer is used, it is sufficient if it is present in amounts of between 10 to 40% based on the volume of the total solution of the polymer, of course, depending upon the particular polymer selected.

In one aspect of this embodiment, the polymer with the optional plasticizer and the ion exchange salt solvent solution are homogeneously blended or admixed and then applied to the conductive substrate. Application can most conveniently be attained by simply dipping the substrate into the ion exchange salt-containing solution or mixture, and then by drying the coating. Suitable coatings can also be formed by spray coating, gaseous deposition, brush application, or any other conventional means.

In another aspect of this embodiment, the ion exchange solution is mixed with a monomer containing solution, and after being coated onto the substrate, the monomer is subjected to polymerizing conditions to form, upon drying, the polymer matrix containing the ion exchange salt therein.

In a still further aspect of this embodiment the polymer and ion exchange salt solution admixture can be coated onto the conductive substrate and then subjected to conventional cross-linking conditions, either catalytically or by use of high energy radiation, to form a very strong, very durable coating.

In a second embodiment of this invention, the conductive substrate is coated with any of a variety of polymeric materials, as mentioned above. A plasticizer may be added, if desired. The polymer is then converted into an ion exchange resin by conventional techniques. For instance, polystyrene can be applied to a conductive substrate, and then reacted with chlorosulfonic acid to produce an ion exchange resin, e.g., the corresponding sulfonated polystyrene.

Other ion exchange resins which can be coated onto the conductive substrate include the cation exchange resins, in which the polymer matrix has incorporated therein sulfonic or carboxylic groups; anion exchange resins in which the polymer has incorporated therein imino-diacetic acid or other chelating functional groups, wherein it contains from 2-6 meq. of exchangeable sites per gram of resin.

In all of these embodiments, the thickness of the coating should be from 0.1 to 20 mils, and preferably from 2 to 10 mils. In general, the thicker the coating, the higher will be the absolute electrical resistance. If the coating is too thin, the ion exchange material may be leached out under the electrolyzing conditions. Within the preferred range, the electrode will exhibit optimum longevity and will not have an excessively high electrical resistance.

All of these electrodes are capable of giving reproducible and rapid responses in the $10^{-1}$ to $10^{-5}$ M range, and particularly in the $10^{-1}$ to $10^{-4}$ M range.

The selection of the particular matrix will depend upon many situation parameters, including the viscosity of the test solution, chemical nature of the test solution, dielectric constant and the like.

The electrodes of this invention were found not only to be as sturdy while less expensive than the conventional prior art barrel type membrane electrodes, but they are more reliable, in some instances giving a steeper linear response when calculated according to the Nernst euqation and in many instances giving a mv response which was in some instances as much as 20 to 30% greater than that of conventional electrodes. Their pH effective range in certain situations was higher, and they have been found to functioning even after a month's continuous use.

Another important advantage of the present coated electrode is that some have been prepared which have lower sensitivity to interfering ions than conventional electrodes. Particularly, it has been found that lower sensitivity to sodium error was exhibited with a calcium electrode formed by the methods of this invention. Moreover, the possible combinations of ion selective electrodes which can be formed by this technique is almost unlimited, so that an entire range of potentiometrically responsive ion electrodes can be produced in inexpensive, compact form.

Another distinctive feature of the electrodes of this invention is that whereas conventional electrodes frequently must be stored in an aqueous medium to prevent changes in the concentration of the reference solution or other damage to the electrode, the coated electrodes of this invention can be stored in air and have a reasonably long and active life.

Having now generally described the invention, a further understanding can be attained by reference to certain specific Examples which are provided herein for purposes of illustration only and are not intended to be limiting unless otherwise specified.

EXAMPLE 1

A 0.018 inch diameter Pt wire was coated with a 6:1 vol. mixture of 5% weight. PVC dissolved in cyclohexanone and 0.1 M calcium didecylphosphate in dioctyl phosphonate. Coating was accomplished by dipping the wire into the mixture several times and allowing to set overnight in air. The remainder of the exposed wire was covered by wrapping it tightly with a paraffin film to prevent direct contact of the metal surface with the test solution.

Although this coated wire electrode gave potential responses to changes in calcium ion activity when placed in solution immediately, best results were obtained after an initial conditioning accomplished by soaking the electrode for about one hour in either distilled water or in a dilute (Ca$\sim 10^{-4}$M)CaCl$_2$ solution.

The performance characteristics of the Ca-coated wire electrode were compared side-by-side with those of the Orion Ca-electrode (Model 92-20). In all cases, the Beckman saturated calomel electrode was used as the reference electrode. The response curve to concentration and activity show two interesting differences. The Orion electrode exhibits a linear response to log $a$ Ca$^{2+}$(slope 30 mv.) in the range of $10^{-1}$ to $10^{-4}$ M Ca, but changes only about 12 mv. from $10^{-4}$M to $10^{-5}$M Ca$^{2+}$. The coated wire electrode shows steeper linear responses to both the logarithmic variation of Ca concentration (slope 31 mv) and of Ca activity (slope 38 mv) than does the Orion barrel electrode. Moreover, the electrode response in the $10^{-4}$ to $10^{-5}$M range, while not Nernstian, is about 25 mv, large enough to extend the useful range to the more dilute solutions.

The pH range of effective use of the coated wire electrode (pH 4.0 to 9.5) is somewhat larger than that of the Orion barrel electrode (4.5-9.0). The coated wire electrode gives a very rapid response time ($\sim$10-15 sec.), can be stored in air, and has a long useful life (some are still functioning after a month's use). A complexometric titration of $10^{-2}$M $Ca^{2+}$ with 0.05M EDTA at pH 9.0 using the coated wire electrode resulted in a sharply defined curve that resembled the one obtained with the Orion barrel electrode, except that the potential reversal beyond the endpoint found in the latter case was absent. This advantage of the coated wire probably results from its lower sensitivity to sodium ions. The response of the Orion barrel electrode in a 0.01 M $Ca^{2+}$ solution changed 5 mv when the solution was made 1 M in NaCl, whereas the coated wire electrode response changed only 0.6 mv, indicating a much higher Ca/Na selectivity ratio.

Interferences of other cations were determined in the following way. For the large interferences (Cu, Pb, Zn) $10^{-3}$M $CaCl_2$ and $10^{-2}$M of the interfering ion were used. For small interferences (Ni, Mg, Ba, Sr) $10^{-4}$M $CaCl_2$ and $10^{-2}$M of the interfering ion were used. In all cases the standard $10^{-3}$M or $10^{-4}$M $CaCl_2$ solutions were adjusted to the same ionic strength as the test solution with NaCl.

The interferences of several cations with the calcium electrode are shown in Table 1 where values of the selectivity coefficients, calculated in the usual manner from the Eisenman equation, are listed. It can be seen that for several cations the coated wire electrode shows considerably less interference than the Orion liquid membrane electrode. In particular, the interference of $Na^+$ and $Mg^{+2}$, $Ni^{+2}$, $Ba^{+2}$ and $Sr^{+2}$ with the coated wire electrode is very small. The interference of $Pb^{2+}$ and more particularly $Zn^{2+}$ are significantly greater than that observed with the Orion electrode.

TABLE 1

Selectivity Coefficients, $K_i$* of Various Divalent Cations

| Interferent | Orion Electrode | Coated Wire Electrode |
|---|---|---|
| $Ni^{2+}$ | 0.026 | 0.0039 |
| $Cu^{2+}$ | 0.24 | 0.15 |
| $Mg^{2+}$ | 0.033 | 0.014 |
| $Ba^{2+}$ | 0.016 | 0.0036 |
| $Sr^{2+}$ | 0.029 | 0.021 |
| $Pb^{2+}$ | 0.23 | 1.86 |
| $Zn^{2+}$ | 1.44 | 32.3 |

*Calculated from $\Delta E = \log(1 + K_i a/a_{Ca})$

EXAMPLES 2-14

An ion association complex solution was prepared by repeatedly shaking a 60 v/v% solution of Aliquat 336S in 1-decanol with an aqueous solution (0.5 M-1.0 M) of the sodium salt of the appropriate anion as shown in Table II below, in order to form the proper quaternary ammonium salt. Phenylalanine and leucine electrodes were prepared with a 30 v/v% Aliquat 336S: decanol solution. Aliquat 336S is a trade name for tricaprylyl methyl ammonium chloride.

A fine platinum wire (0.01-0.02 inch diameter) was coated with polyvinyl chloride (PVC) by one of two methods. For the phenylalanine and leucine electrodes, the wire was dipped into a 15 w/v% PVC in cyclohexanone solution, allowed to reach near dryness (about 30 minutes) and then soaked for 1 to 2 hours in the previously prepared association complex solution in decanol. For the other electrodes the wire was coated with a 10:1 mixture of 8 w/v% PVC: cyclohexanone and the decanol solution of the complex and the coating was allowed to dry thoroughly (about 1 hour). In both cases, the remainder of the exposed wire was wrapped tightly with a paraffin film to prevent direct contact of the metal surface with the test solution. The electrode was initially conditioned by soaking in a $10^{-1}$M solution of the anion to be measured for 15 minutes. The electrode was stored in air between use and reconditioned immediately before using by soaking for 5 minutes in a $10^{-1}$M solution. All the electrodes were found to be functional even after three months of use.

An Orion pH meter, Model 701, was used for all measurements and a Beckman saturated calomel electrode served as the reference electrode.

The electrodes were first tested in pure solutions of the appropriate salts. Equilibrium potentials were achieved within a few seconds and were reproducible to ±0.5 mv or better. The potential response was linear with the logarithm of anion activity from $10^{-1}$ to at least $10^{-2.6}$M, although the useful concentration range was usually $10^{-1}$ to $10^{-4}$M. This information is summarized in Table I.

The electrodes require daily restandardization, as was necessary for the conventional electrodes of similar composition.

Interferences by other anions were determined by adding a sufficient amount of the interfering anion to a $10^{-3}$ or $4 \times 10^{-3}$M standard test solution to give a potential difference of from 10 to 100 mv from the pure test solution. Selectivity coefficients were calculated from the Eisenman equation:

$$\Delta E = \text{slope} \log \left[ 1 + Ki \frac{a_i^{n/z}}{a_A} \right]$$

where $a_i$ and $a_A$ are the activities of the interfering anion and electrode anion in the test solution, respectively. When the concentration of the interfering anion used was large enough to change the activity of the test anion, appropriate corrections were applied. For these cases $\Delta E$ was given by:

$$\Delta E = \Delta E_{measured} + \text{slope} (\Delta \log a_A)$$

where $\Delta \log a_A$ is the difference in the logarithm of the activity of the electrode anion in the two solutions. The interferences, expressed as selectivity coefficients, of several anions are shown in Table II below for both the coated wire electrodes and the liquid-membrane electrodes. It is interesting to note that the coated wire electrodes gave greater selectivity, i.e., lower $K_i$ values, in almost every case.

TABLE II

| Example | Electrode | Slope (mv/log a) | Concentration range of linear response (M) | Useful Concentration range (M) |
|---|---|---|---|---|
| 2 | Perchlorate | 58 | $10^{-1} - 10^{-1}$ | $10^{-1} - 10^{-4}$ |
| 3 | Chloride | 55 | $10^{-1} - 10^{-4}$ | $10^{-1} - 10^{-4}$ |
| 4 | Bromide | 59 | $10^{-1} - 10^{-3}$ | $10^{-1} - 10^{-4}$ |
| 5 | Iodide | 60 | $10^{-1} - 10^{-4}$ | $10^{-1} - 10^{-4}$ |
| 6 | Thiocyanate | 59 | $10^{-1} - 10^{-3}$ | $10^{-1} - 10^{-4}$ |
| 7 | Oxalate | 28* | $10^{-1} - 10^{-4}$ | $10^{-1} - 10^{-4}$ |
| 8 | Acetate | 50* | $10^{-1} - 10^{-3}$ | $10^{-1} - 10^{-4}$ |
| 9 | Benzoate | 53* | $10^{-1} - 10^{-3}$ | $10^{-1} - 10^{-4}$ |
| 10 | Sulfate | 28 | $10^{-1} - 10^{-3}$ | $10^{-1} - 10^{-4}$ |
| 11 | Salicylate | 53* | $10^{-1} - 10^{-3}$ | $10^{-1} - 10^{-3}$ |
| 12 | Phenylalanine | 54* | $10^{-1} - 10^{-2.6}$ | $10^{-1} - 10^{-3}$ |
| 13 | Leucine | 52* | $10^{-1} - 10^{-2.6}$ | $10^{-1} - 10^{-3}$ |
| 14 | Nitrate | 55* | $10^{-1} - 10^{-3}$ | $10^{-1} - 10^{-5}$ |

*log C

TABLE III

Selectivity Coefficients, $K_{ji}$ For the Coated Wire Electrodes Compared to These For the Liquid-Membrane Electrodes

| Electrode | Chloride | | Interfering Anion Nitrate | | Sulfate | | Miscellaneous | |
|---|---|---|---|---|---|---|---|---|
| Perchlorate | 0.004 | (0.18) | 0.028 | (0.12) | <0.001 | <0.001 | $IO_3^-$, 0.039 | (0.20) |
| Chloride | — | | 2.0 | (3.0) | 0.12 | (0.001) | $Br^-$, 1.2 | (2.7) |
| Bromide | 0.19 | (0.40) | 2.0 | (1.1) | 0.020 | (<0.001) | $I^-$, 14.5 | (3.6) |
| Iodide | 0.0048 | (0.004) | 0.11 | (0.23) | <0.001 | (<0.001) | $Br^-$, 0.056 | (0.22) |
| Thiocyanaic | <0.001 | (<0.001) | <(0.046 | (0.007) | 0.001 | (0.010) | $I^-$, 0.34 | (0.42) |
| Benzoate | 1.3 | (0.17) | 1.3 | (0.48) | 0.15 | (<0.001) | Salicylate 1.4 | (0.29) |
| Salicylate | <0.001 | (<0.001) | 0.42 | (0.030) | <0.001 | (<0.001) | m-OH benzoate 0.22 | (0.1) |
| Oxalate | 51 | ($\approx$80) | — | | 1.3 | | OAc 11 | (11) |
| Sulfate | 16 | (100) | 30 | (820) | — | | | |
| Phenylalanine | 0.8 | (1) | 2 | (1.6) | 0.01 | (0.1) | Gly, 0.025 | (0.040) |
| | | | | | | | Leu, 0.13 | (0.40) |
| Leucine | 0.50 | (0.50) | 0.50 | (0.30) | 0.020 | (0.025) | Gly, 0.032 | (0.063) |
| | | | | | | | Val, 0.25 | (0.25) |
| | | | | | | | Phe, 2.0 | (1.6) |
| Citrate | 0.04 | (0.23) | — | | 0.001 | (0.002) | $ClO_3$, 1.7 | (0.89) |
| | | | | | | | $NO_2$, 0.18 | ($\sim$0.5) |

*Value of $K_j$ for liquid membrane electrode is in parenthesis.

EXAMPLE 15

A fine platinum wire was coated with polystyrene which was dissolved in a chloroform solution. When the coating was dry, the coated wire was placed in chlorosulfonic acid at room temperature for 5 minutes, removed, washed with water, and then soaked in a solution containing the cation of interest for two hours. In this example the cation of interest was copper ion and the soaking solution was 0.1M copper sulfate.

Tabulated below are the millivolt responses for solutions of various copper ion concentrations.

| Concentration of Copper Ion | Millivolt Response |
|---|---|
| $10^{-1}$ | 466 |
| $10^{-2}$ | 448 |
| $10^{-3}$ | 429 |
| $10^{-4}$ | 410 |

The slope found here is about 24 mv which is fairly close to the theoretical Nernstian slope (29 mv).

A similar electrode was prepared in which the soaking period in chlorosulfonic acid was only 40 seconds and the following results were obtained:

| Concentration of Copper Ion | Millivolt Response |
|---|---|
| $10^{-1}$ | 407 |
| $10^{-2}$ | 392 |
| $10^{-3}$ | 372 |
| $10^{-4}$ | 353 |
| $10^{-5}$ | 342 |

Having fully described the invention, it will be apparent to one of ordinary skill in the art that many changes and modifications can be made thereto without departing from the spirit or scope thereof.

What is claimed as new and intended to be covered by Letters Patent is:

1. In a process for measuring the potentiometric responses caused by ion activity changes in solution, the improvement which comprises:
   using an electrode formed by coating an ion exchange material which is molecularly dispersed throughout an insoluble film-forming polymeric matrix directly onto a conductive substrate such that an oxidation-reduction mechanism is not operative in the response of said electrode to the activity of ions in said solutions.

2. The process of claim 1, wherein said ion exchange material in said polymeric matrix is an ion exchange resin.

3. The process of claim 2, wherein said ion exchange resin is sulfonated polystyrene.

4. The process of claim 2, wherein said ion exchange resin is characterized by 2-6 meq. of exchangeable sites per gram of resin.

5. The process of claim 1, wherein said conductive substrate is in the form of a conductive wire.

6. The process of claim 1, wherein said dispersion of ion exchange material in said polymeric matrix is a colloidal dispersion or a true solution of ion exchange material in a polymeric matrix.

7. The process of claim 6, wherein said ion exchange material is dispersed in said polymeric matrix in an amount of from 1-25% by weight based on the total weight.

* * * * *